US012611199B2

(12) United States Patent
Hung

(10) Patent No.: US 12,611,199 B2
(45) Date of Patent: Apr. 28, 2026

(54) METHOD AND SYSTEM FOR OVULATION DETECTION IN FEMALE'S MENSTRUAL CYCLES BASED ON HEART RATE VARIABILITY ANALYSIS

(71) Applicant: MING CHI UNIVERSITY OF TECHNOLOGY, New Taipei City (TW)

(72) Inventor: Wei-Wen Hung, New Taipei City (TW)

(73) Assignee: MING CHI UNIVERSITY OF TECHNOLOGY, New Taipei City (TW)

( * ) Notice: Subject to any disclaimer, the term of this patent is extended or adjusted under 35 U.S.C. 154(b) by 286 days.

(21) Appl. No.: 18/631,099

(22) Filed: Apr. 10, 2024

(65) Prior Publication Data

US 2024/0398390 A1    Dec. 5, 2024

(30) Foreign Application Priority Data

Jun. 5, 2023    (TW) ................................. 112120918

(51) Int. Cl.
| | |
|---|---|
| *A61B 10/00* | (2006.01) |
| *A61B 5/024* | (2006.01) |
| *A61B 5/0245* | (2006.01) |
| *A61B 5/347* | (2021.01) |
| *A61B 5/352* | (2021.01) |

(52) U.S. Cl.
CPC ...... *A61B 10/0012* (2013.01); *A61B 5/02416* (2013.01); *A61B 5/02438* (2013.01); *A61B 5/0245* (2013.01); *A61B 5/347* (2021.01); *A61B 5/352* (2021.01)

(58) Field of Classification Search
None
See application file for complete search history.

(56) References Cited

U.S. PATENT DOCUMENTS

| | | | | |
|---|---|---|---|---|
| 2016/0058428 | A1* | 3/2016 | Shinar .................. | A61B 5/7267 |
| | | | | 600/301 |
| 2018/0035982 | A1* | 2/2018 | Tholen ............... | A61B 10/0012 |
| 2020/0000441 | A1* | 1/2020 | Lafon ................ | A61B 5/02438 |
| 2022/0313223 | A1* | 10/2022 | Thigpen .............. | A61B 5/4343 |
| 2023/0248320 | A1 | 8/2023 | Lafon et al. | |

* cited by examiner

*Primary Examiner* — Etsub D Berhanu
(74) *Attorney, Agent, or Firm* — LANWAY IPR SERVICES; Chun-Ming Shih

(57) ABSTRACT

This invention relates to a method and system for detecting ovulation in female's menstrual cycles, which involves collecting menstrual cycle information of a subject to calculate ovulation interval dates. Daily heart rate waveform signals are used to obtain heart rate-related physiological parameters, including the first cumulative power (LF), second cumulative power (HF), standard deviation of interbeat intervals (SDNN), root mean square of successive differences (RMSSD), cumulative power ratio (LF/HF), and heart rate parameter ratio (SDNN/RMSSD). The invention selects the day with the highest cumulative power ratio (LF/HF) and heart rate parameter ratio (SDNN/RMSSD) within the ovulation interval as the day of ovulation.

10 Claims, 5 Drawing Sheets

Obtain the subject's menstrual cycle information — S110

Calculate an ovulation interval date — S120

Measure a heart rate waveform signal of the subject — S130

Obtain a first cumulative power (LF), a second cumulative power (HF), a standard deviation of the heartbeat interval (SDNN), and a root mean square of the sum of the squares of adjacent differences (RMSSD) from the heart rate waveform signal. — S140

Divide the first cumulative power by the second cumulative power to obtain a cumulative power ratio (LF/HF) — S150

Select the day with the maximum cumulative power ratio (LF/HF) and heart rate parameter ratio (SDNN/RMSSD) from the ovulation interval date as the ovulation day — S160

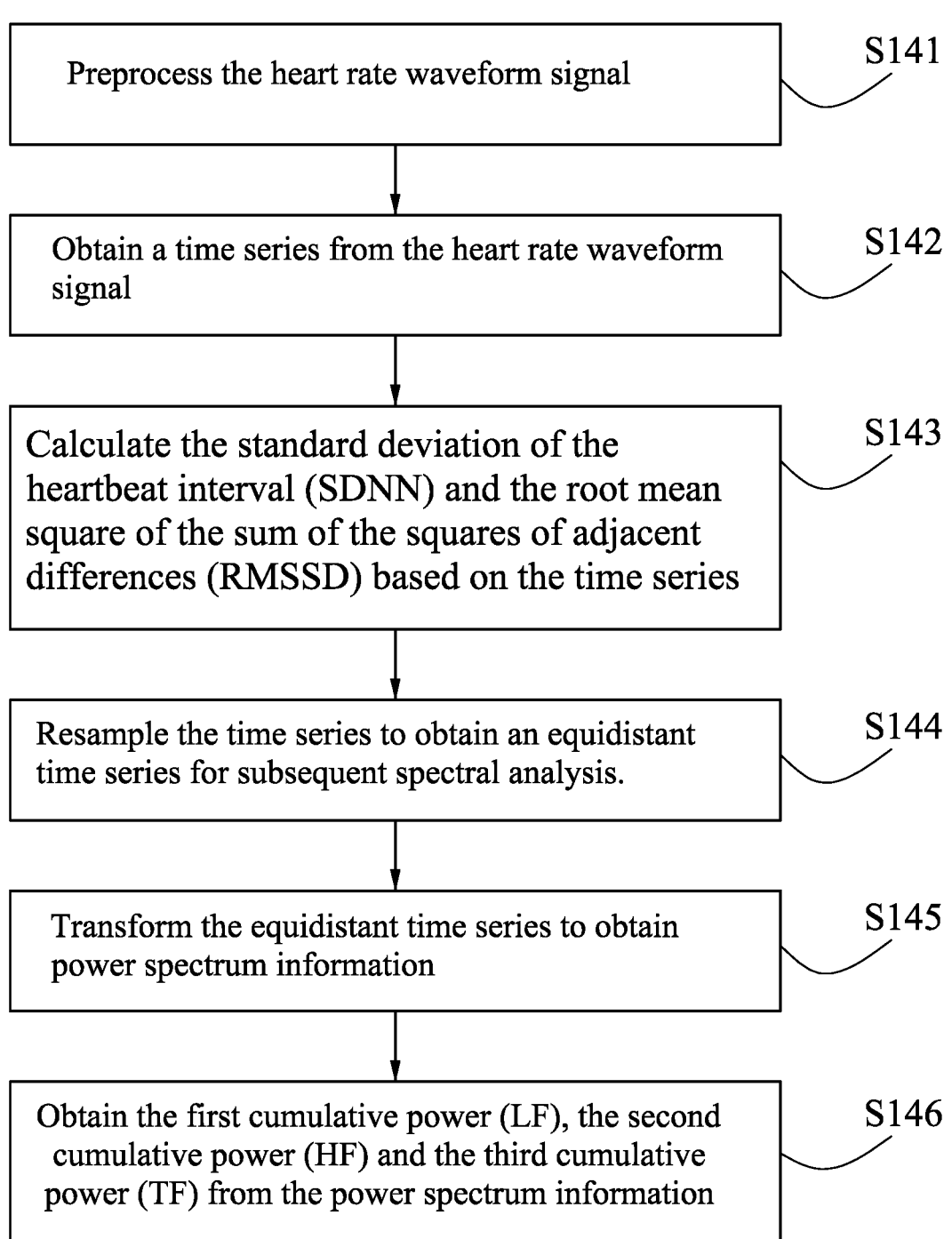

Preprocess the heart rate waveform signal    S141

Obtain a time series from the heart rate waveform signal    S142

Calculate the standard deviation of the heartbeat interval (SDNN) and the root mean square of the sum of the squares of adjacent differences (RMSSD) based on the time series    S143

Resample the time series to obtain an equidistant time series for subsequent spectral analysis.    S144

Transform the equidistant time series to obtain power spectrum information    S145

Obtain the first cumulative power (LF), the second cumulative power (HF) and the third cumulative power (TF) from the power spectrum information    S146

FIG. 2

METHOD AND SYSTEM FOR OVULATION DETECTION IN FEMALE'S MENSTRUAL CYCLES BASED ON HEART RATE VARIABILITY ANALYSIS

FIELD OF THE DISCLOSURE

The invention relates to a method for detecting ovulation in women, specifically a method based on the analysis of heart rate variability for the detection of ovulation during the menstrual cycle.

BACKGROUND OF THE INVENTION

Menstruation is a physiological phenomenon in women that also reflects the health condition of a woman's body. To fully grasp the menstrual health status of women, several common methods for detecting the ovulation date are available, with the most common methods as follows:

1. Ovulation Date Calculation Method: This is the simplest method, requiring no special equipment or expenses. It assumes a 28-day cycle for every woman, with ovulation occurring on the 14th day. However, this does not apply to all women. The accuracy of this method may decrease due to irregular cycles.
2. Basal Body Temperature Measurement: By observing body temperature, one can monitor and understand their cycle regularity at a relatively low cost. However, it requires daily measurement at the same time and may be affected by sleep duration, illness, and other factors.
3. Cervical Mucus Method: This involves observing cervical secretions to determine ovulation, requiring no special equipment or techniques and can be observed at any time. However, it requires daily observation of changes and can be influenced by many factors, such as severe vaginal infection, vaginal douching, vaginal secretions during sexual arousal, post-coital mucus, and the use of spermicidal drugs in the vagina.
4. Ovulation Predictor Kits: Convenient and relatively accurate, these kits test urine for ovulation, allowing for home testing. However, they are comparatively expensive, and irregular cycles can lead to failed tests, necessitating multiple tests.
5. Blood Test for Progesterone Levels: By drawing blood, this method is very accurate in measuring the concentration of progesterone to determine ovulation. However, it is inconvenient as it requires waiting for a report and cannot provide immediate results.
6. Vaginal Ultrasound: Currently the most direct and accurate method, it allows for the observation of follicle maturation and rupture. Similar to blood tests, it requires a visit to a medical laboratory or hospital, making it inconvenient and costly.
7. Saliva Ferning Test: A simple, inexpensive, and non-invasive method that requires a specific microscope for observation. However, its accuracy can be affected by various factors such as the quality and quantity of saliva and the difficulty of interpreting results.

In summary, while there are many methods available for examining ovulation in women, each has its drawbacks. Therefore, providing a more accurate and convenient method for ovulation detection is a worthwhile consideration for those with general knowledge in this field.

SUMMARY OF THE INVENTION

The present invention provides a method for detecting ovulation in a female's menstrual cycle, utilizing physiological parameters from heart rate waveform signals, such as the standard deviation of interbeat intervals (SDNN), the root mean square of successive differences (RMSSD), and frequency domain parameters of heart rate variability, LF and HF, to detect the ovulation day. This offers a more accurate and convenient testing method with specific technical means as follows:

A method for detecting ovulation during a female's menstrual cycle begins by obtaining the first day of a subject's menstrual period, the longest and shortest menstrual cycle lengths. An ovulation interval date is then calculated based on these lengths. Daily measurements of the subject's heart rate waveform signal are taken. From this signal, a first cumulative power (LF), a second cumulative power (HF), a standard deviation of interbeat intervals (SDNN), and a root mean square of successive differences (RMSSD) are obtained. The sampling frequency range of the second cumulative power is greater than that of the first cumulative power. Next, a cumulative power ratio (LF/HF) is obtained by dividing the first cumulative power by the second cumulative power, and a heart rate parameter ratio (SDNN/RMSSD) by dividing the standard deviation of interbeat intervals by the root mean square of successive differences. Finally, the day within the ovulation interval when both the cumulative power ratio (LF/HF) and the heart rate parameter ratio (SDNN/RMSSD) are at their highest is selected as the ovulation day.

Additionally, the ovulation detection method includes steps such as preprocessing the heart rate waveform signal, obtaining interval times between adjacent peaks in the heart rate waveform signal to form a time series, calculating the SDNN and RMSSD based on this time series, resampling the time series to obtain an equidistant time series, transforming the equidistant time series to obtain power spectrum information, and obtaining the first (LF) and second (HF) cumulative powers from the power spectrum information. The second cumulative power's sampling frequency range exceeds that of the first cumulative power.

For this ovulation detection method, the first cumulative power's sampling frequency range is 0.04-0.15 Hz, and the second cumulative power's sampling frequency range is 0.15-0.4 Hz. The method also includes sampling a third cumulative power (TF) within a 0.04-0.4 Hz frequency range and calculating the percentages of the first (LF %) and second (HF %) cumulative powers using specific formulas. The Berger algorithm is used for resampling the time series, and the Discrete Fourier Transform is applied for transforming the equidistant time series. The specific formulas are listed below:

$$LF\% = \frac{LF}{TF} \times 100\%;$$

$$HF\% = \frac{HF}{TF} \times 100\%;$$

If the longest and shortest menstrual cycle lengths cannot be obtained, the longest cycle length is assumed to be 35 days, and the shortest cycle length, 21 days. The start and end dates of the ovulation interval are determined by subtracting specific days from the shortest and longest cycle lengths, respectively. In one embodiment, the shortest cycle length of the menstrual cycle is subtracted by 18 days to serve as the start date of the ovulation interval date, and the longest cycle length of the menstrual cycle is subtracted by 11 days to serve as the end date of the ovulation interval date.

This invention also provides a system for detecting ovulation during a female's menstrual cycle, applicable to a subject. The ovulation detection system comprises a heart rate waveform measuring device and a computing device. The heart rate waveform measuring device is configured to provide a heart rate waveform signal. The computing device, connected to the heart rate waveform measuring device, includes an input module, a first calculation module, a second calculation module, and a third calculation module. The input module is designed for inputting the first day of the menstrual cycle, the longest and shortest cycle lengths. The first calculation module is capable of calculating an ovulation interval date based on the first day, the longest and shortest cycle lengths. The second calculation module is tasked with calculating a first cumulative power (LF), a second cumulative power (HF), a standard deviation of interbeat intervals (SDNN), a root mean square of successive differences (RMSSD), a cumulative power ratio (LF/HF), and a heart rate parameter ratio (SDNN/RMSSD) based on the heart rate waveform signal. The third calculation module is responsible for calculating the ovulation day within the ovulation interval based on the cumulative power ratio (LF/HF) and the heart rate parameter ratio (SDNN/RMSSD). This module selects the day when both ratios reach their maximum values as the day of ovulation.

In the described ovulation detection system, the second calculation module processes the heart rate waveform signal to obtain a time series and calculates the standard deviation of interbeat intervals (SDNN) and the root mean square of successive differences (RMSSD). It is also configured to resample and transform the time series to acquire power spectrum information, from which it obtains the first cumulative power (LF) and the second cumulative power (HF), where the sampling frequency range of the second cumulative power is greater than that of the first cumulative power.

The foregoing, as well as additional objects, features and advantages of the invention will be more readily apparent from the following detailed description, which proceeds with reference to the accompanying drawings.

BRIEF DESCRIPTION OF THE DRAWINGS

FIG. 2 illustrates a method of calculating parameters;

DESCRIPTION OF THE PREFERRED EMBODIMENTS

Figure 1:
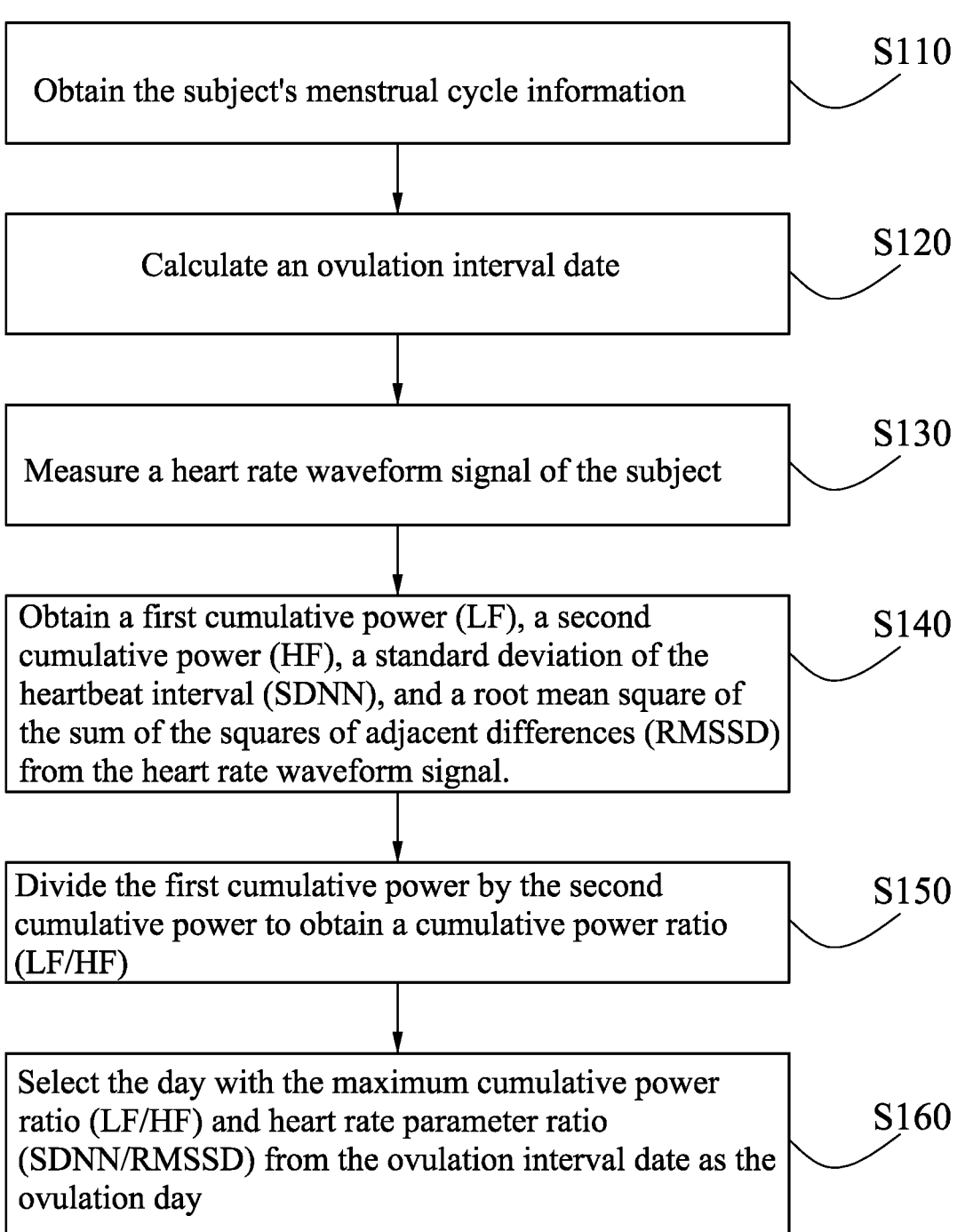
FIG. 1 illustrates a method of ovulation detection during the menstrual cycle of this disclosure.

Please refer to FIG. 1, which illustrates the method of ovulation detection during the menstrual cycle of this disclosure. First, step S110 is performed to obtain the first day of a menstrual cycle, the longest cycle length of a menstrual cycle, and the shortest cycle length of a menstrual cycle of the subject. In step S110, it is necessary to obtain the subject's menstrual cycle information, including the first day of the menstrual cycle, the longest cycle length of the menstrual cycle (L_max), and the shortest cycle length of the menstrual cycle (L_min), which can be used to calculate a possible ovulation interval date. Among them, the first day of the menstrual cycle is the information that will be used as the basis for subsequent calculations and judgments, and the longest and shortest cycle lengths of the menstrual cycle are related to the ovulation interval date. In addition, if the subject cannot provide accurate longest and shortest cycle lengths of the menstrual cycle, the shortest cycle length of the menstrual cycle will be set to 21 days (L_min=21), and the longest cycle length of the menstrual cycle will be set to 35 days (L_max=35). Specifically, the first day of the menstrual cycle, the longest cycle length of the menstrual cycle (L_max), and the shortest cycle length of the menstrual cycle (L_min) can be entered into a calculation device.

Then, step S120 is performed to calculate an ovulation interval date based on the longest and shortest cycle lengths of the menstrual cycle. Specifically, the shortest cycle length of the menstrual cycle is subtracted by 18 days to serve as the start date of the ovulation interval (OV_start), and the longest cycle length of the menstrual cycle is subtracted by 11 days to serve as the end date of the ovulation interval (OV_end). In addition, the ovulation interval date can be calculated by the calculation device. In other words, the ovulation interval date is from the OV_start day to the OV_end day. The calculation formula is as follows:

$$OV\_start = L\_min - 18$$
$$OV\_end = L\_max - 11$$

Then, step S130 is performed to measure a heart rate waveform signal of the subject every day. Specifically, a heart rate waveform measurement device is used to measure the heart rate waveform signal, and these heart rate waveform signals can be collected in a contact or non-contact manner. The contact method includes using an electrocardiogram (ECG) or a photoplethysmogram (PPG) to measure the heart rate waveform signal. The electrocardiogram is a common medical device that detects and records changes in the heart's electrical potential by attaching electrodes to the surface of the human skin. The photoplethysmogram is a photoelectric technology that detects changes in blood volume by observing the degree of reflection of incident light on the skin and analyzing the phenomenon of light attenuation of the skin.

The non-contact method includes using image signal processing technology, mainly by analyzing the changes in the grayscale of the skin image to collect the heart rate waveform signal when the heart contracts and relaxes. For example, using a general camera or a mobile phone lens to obtain continuous images of the face or fingertip, detecting changes in the grayscale of the skin image, and collecting the heart rate waveform signal under the contraction and relaxation of the heart.

Afterwards, step S140 is performed to obtain a first cumulative power (LF), a second cumulative power (HF), a standard deviation of the heartbeat interval (SDNN), and a root mean square of the sum of the squares of adjacent differences (RMSSD) from the heart rate waveform signal. The sampling frequency range of the second cumulative power is greater than the sampling frequency range of the first cumulative power. That is, the first cumulative power (LF), the second cumulative power (HF), the standard deviation of the heartbeat interval (SDNN), and the root mean square of the sum of the squares of adjacent differences (RMSSD) are calculated from the heart rate waveform signal, and these parameters can be obtained by further calculation from the heart rate waveform signal by the calculation device.

Among them, the first cumulative power is the cumulative power of the low-frequency band (LF). LF is mainly an indicator of the joint regulation of the sympathetic and parasympathetic nerves. That is, LF reflects the combined effect of these two types of nerve activity. The sympathetic and parasympathetic nerves are the two major parts of the autonomic nervous system, responsible for regulating the activity of various organs and systems in the body, including the heart, lungs, digestive system, etc.

The second cumulative power is the cumulative power in the high-frequency band (HF), which is mainly an indicator of the activity of the parasympathetic nerve. The parasympathetic nerve is mainly responsible for the body's rest and digestive activities, such as lowering the heart rate and increasing gastrointestinal motility. Therefore, changes in HF can be used to understand the activity status of the parasympathetic nerve.

Furthermore, the third cumulative power (TF) also has to be measured, which represents the total activity of the sympathetic and parasympathetic nerves. This indicator reflects the overall state of the autonomic nervous system and can be used to assess the body's stress response, rest state, etc. The third cumulative power can be used to calculate the percentage of the first cumulative power (LF %) and the percentage of the second cumulative power (HF %). The calculation formula is as follows:

$$LF\% = \frac{LF}{TF} \times 100\%;$$

$$HF\% = \frac{HF}{TF} \times 100\%;$$

The standard deviation of the heartbeat interval (SDNN) and the root mean square of the sum of the squares of adjacent differences (RMSSD) are indicators of the variation of the heartbeat interval. Among them, a larger SDNN indicates a larger variation in the heartbeat interval, reflecting the overall activity of the autonomic nervous system. A larger RMSSD indicates a larger variation in the heartbeat interval, which is generally considered to indicate stronger parasympathetic nerve activity. Conversely, if RMSSD is smaller, it indicates stronger sympathetic nerve activity.

In step S140, the first cumulative power (LF), the second cumulative power (HF), the standard deviation of the heartbeat interval (SDNN), and the root mean square of the sum of the squares of adjacent differences (RMSSD) are obtained by transforming and analyzing the heart rate waveform signal. The specific method is as follows:

Please refer to FIG. 2, which illustrates the method of calculating parameters. First, step S141 is performed to preprocess the heart rate waveform signal. Preprocessing includes signal amplification, filtering, smoothing, analog signal sampling conversion to digital signal, and digital signal drift processing. These processes can remove noise and interference in the signal and improve the quality of the signal.

Then, step S142 is performed to obtain the interval time between adjacent peaks from the heart rate waveform signal and form a time series. Specifically, a peak detection algorithm is used to mark the peak positions of the R wave in the heart rate waveform signal and generate a sequence of interval times between adjacent peaks of the heart rate waveform signal.

Then, step S143 is performed to calculate the standard deviation of the heartbeat interval (SDNN) and the root mean square of the sum of the squares of adjacent differences (RMSSD) based on the time series. Specifically, time-domain analysis is performed on the time series to further calculate the heart rate (HR), heart rate variability information, and the average value of the time interval between adjacent peaks of the R wave (RR_mean). The heart rate (HR) is an indicator that describes the speed of the heartbeat, generally expressed in beats per minute (bpm). The following formulas are used to calculate SDNN and RMSSD:

$$HR = \frac{60}{RR_{mean}} \text{ (bpm)};$$

$$RR_{mean} = \frac{1}{N} \cdot \sum\nolimits_{i=1}^{N}(RR_i);$$

$$SDNN = \sqrt{\frac{1}{N} \cdot \sum\nolimits_{i=1}^{N}(RR_i - RR_{mean})^2};$$

$$RMSSD = \sqrt{\frac{1}{(N-1)} \cdot \sum\nolimits_{i=1}^{N-1}(RR_{i+1} - RR_i)^2};$$

$$RMSSD\% = \frac{RMSSD}{SDNN + RMSSD} \times 100\%\circ$$

Here, RRi represents the time interval between the i-th pair of adjacent R-wave peaks, and N represents the number of pairs of adjacent R-wave peaks included in the calculation of heart rate variability (HRV).

Next, proceed to step S144, resample the time series to obtain an equidistant time series for subsequent spectral analysis. Specifically, the Berger algorithm is used for resampling. The Berger algorithm can refer to the original technical literature: Berger, R. D., Akselrod, S., Gordon, D., and Cohen, R. J., "An Efficient Algorithm for Spectral Analysis of Heart Rate Variability," IEEE Transactions on Biomedical Engineering, Vol. 33, pp. 900-904, 1986.

Figure 3:
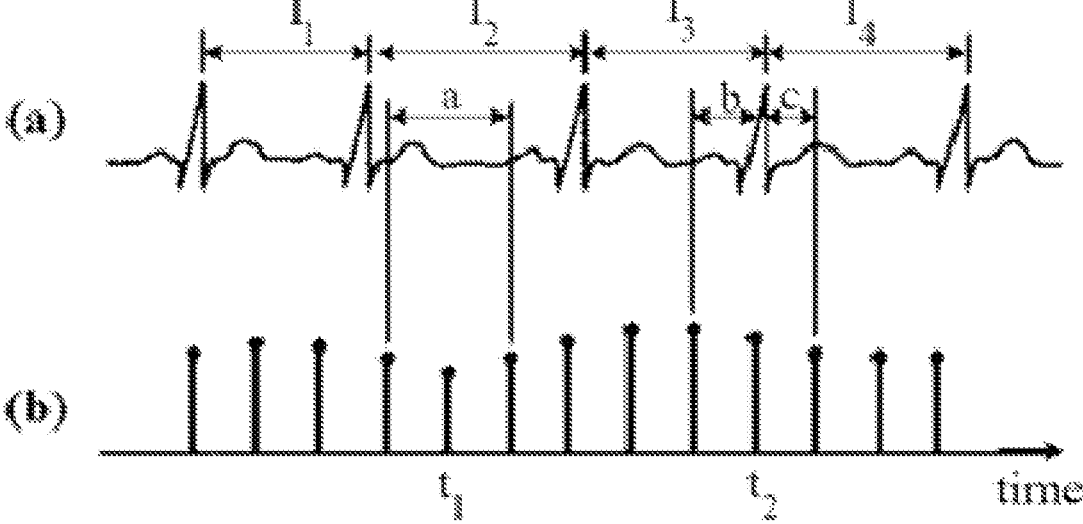
FIG. 3 illustrates a schematic diagram of resampling.

Please refer to FIG. 3, which is a schematic diagram of resampling. Among them, (a) is the heart rate waveform signal before resampling, and (b) is the equidistant time series after resampling by the Berger algorithm. First, the sampling frequency is reduced from 100 Hz to 4 Hz, and then a local window is defined. The local window will include the range of the resampled sampling points and their previous and next sampling points on the time axis. That is, the range of the local window is determined by the resampled sampling points.

Next, it is necessary to determine the amplitude of each resampled sampling point. There are two situations here: The first situation is when the sampling point is at time point t1, at this time the local window falls completely within a time interval I2. In this case, the amplitude of the sampling point is set to a/I2. The second situation is when the sampling point is at time point t2, at this time the local window spans two time intervals I3 and I4. In this case, the amplitude of the sampling point is set to b/I3+c/I4. In this way, an adjacent peak-to-peak interval time series with equal time intervals can be obtained after resampling, that is, an equidistant time series.

Then return to FIG. 2, after obtaining the equidistant time series, proceed to step S145, transform the equidistant time series to obtain power spectrum information. Specifically, the discrete Fourier transform (DFT) is used for the transformation.

After obtaining the power spectrum information, proceed to step S146, obtain the first cumulative power (LF), the second cumulative power (HF) and the third cumulative power (TF) from the power spectrum information, and calculate the first cumulative power percentage (LF %) and the second cumulative power percentage (HF %). Specifically, the first cumulative power (LF), the second cumulative power (HF) and the third cumulative power (TF) are obtained through different sampling frequency ranges. In this embodiment, the sampling frequency ranges are 0.04-0.15 Hz (LF), 0.15-0.4 Hz (HF), and 0.04-0.4 Hz (TF). The calculation methods of the first cumulative power percentage (LF %) and the second cumulative power percentage (HF %) are as follows:

$$LF\% = \frac{LF}{TF} \times 100\%;$$

$$HF\% = \frac{HF}{TF} \times 100\%;$$

After the above steps, parameters such as LF, LF %, HF, HF %, SDNN and RMSSD can be obtained, which can be used for subsequent ovulation day tests. The above steps S141~S146 can be realized through a computing device to further calculate parameters such as LF, LF %, HF, HF %, SDNN and RMSSD.

Please refer back to FIG. 1, then proceed to step S150, divide the first cumulative power by the second cumulative power to obtain a cumulative power ratio (LF/HF), and divide the standard deviation of the heartbeat interval by the root mean square of the adjacent difference sum of squares to obtain a heart rate parameter ratio (SDNN/RMSSD), which can be calculated by the computing device to calculate the cumulative power ratio (LF/HF) and the heart rate parameter ratio (SDNN/RMSSD). Specifically, the following formulas are used for calculation:

$$LF/HF = \frac{LF}{HF}$$

$$SDNN/RMSSD = \frac{SDNN}{RMSSD}$$

LF and HF respectively represent the low-frequency and high-frequency cumulative power in the analysis of heart rate variability. LF and HF correspond to the joint activity of the sympathetic and parasympathetic nerves and the activity of the parasympathetic nerves. The ratio of these two (LF/HF) is used as an indicator of autonomic balance in some medical research, and is considered to reflect the relative activity of the sympathetic and parasympathetic nerves. If this ratio is higher, it indicates that the sympathetic nerve activity is stronger; if this ratio is lower, it indicates that the parasympathetic nerve activity is stronger.

SDNN refers to the standard deviation of normal heartbeat intervals, which represents the overall activity index of the autonomic nerves. RMSSD is the root mean square of the sum of squares of the differences between adjacent normal heartbeat intervals. The higher the value, the stronger the parasympathetic nerve activity. The ratio of these two (SDNN/RMSSD) can be used to evaluate the relative activity of the sympathetic and parasympathetic nerves.

After calculating the cumulative power ratio and heart rate parameter ratio, proceed to step S160, select the day with the maximum cumulative power ratio (LF/HF) and heart rate parameter ratio (SDNN/RMSSD) from the ovulation interval date as the ovulation day.

Specifically, it is necessary to make judgments from several conditions, including time domain conditions, frequency domain conditions, adjacent date conditions and filtering conditions. The time domain condition is related to the heart rate parameter ratio. The RMSSD % value of the ovulation date is smaller, and the heart rate parameter ratio (SDNN/RMSSD) is larger. This is because during ovulation, the activity of the parasympathetic nerve (measured by RMSSD %) usually decreases, while the activity of the sympathetic nerve (measured by SDNN/RMSSD) usually increases.

The frequency domain condition is related to the cumulative power ratio. The HF % value of the ovulation date is smaller, and the cumulative power ratio (LF/HF) is larger. This is also based on the fact that during ovulation, the activity of the parasympathetic nerve (measured by HF %) usually decreases, while the activity of the sympathetic nerve (measured by LF/HF) usually increases.

The adjacent date condition is related to the day before or after the ovulation date. The RMSSD % value of the day before or after the ovulation date is smaller, and its heart rate parameter ratio (SDNN/RMSSD) is larger; at the same time, its HF % value is smaller, and its cumulative power ratio (LF/HF) is larger. This is because ovulation is usually a process and is not limited to one day, so considering adjacent dates also has similar physiological changes.

The filtering condition is to exclude non-ovulation days. If on a day within the "ovulation interval date", its heart rate parameter ratio (SDNN/RMSSD) is less than 1.0, or its cumulative power ratio (LF/HF) is less than 1.0, then this day will be excluded first. This is because in these cases, the activity of the parasympathetic nerve is stronger than that of the sympathetic nerve, so it is considered a non-ovulation day.

In another embodiment, an algorithm can be established to calculate the ovulation date by the computing device, and further implement step S150. The specific method is as follows:

Score the ovulation interval dates (every day from the OV_start day to the OV_end day after the start of menstruation), and finally find the date with the highest score as the estimated ovulation date.

Sort all the dates within the ovulation interval, sort the values of the four physiological parameters (RMSSD %, SDNN/RMSSD, HF %, LF/HF), and find the top three with the smallest RMSSD %, HF % and the top three with the biggest SDNN/RMSSD, LF/HF. This can understand which dates' physiological parameters are closest to the expected ovulation day characteristics within this interval.

Then exclude the unlikely ovulation dates. If on a day within the ovulation interval, its heart rate parameter ratio (SDNN/RMSSD) is less than 1.0, or its cumulative power ratio (LF/HF) is less than 1.0, and give it-5 points to exclude this day.

For the dates with the smallest RMSSD %, HF % and the biggest SDNN/RMSSD, LF/HF, give 3, 2, 1 points respectively. In addition, if the adjacent date (the day before or after) of a day is also ranked in the top three when taking the smallest RMSSD %, HF % and the biggest SDNN/RMSSD, LF/HF, give 1 point to that date. This is because ovulation does not occur on a single day, and the physiological parameters of its adjacent dates are considered.

In detail, for the dates with the smallest RMSSD % values within the ovulation interval, give 3, 2, 1 points respectively. If the RMSSD % value of the adjacent date (the day before or after) of a day is also in the top three, give 1 point to that date.

For the dates with the biggest SDNN/RMSSD ratio within the ovulation interval, give 3, 2, 1 points respectively. If the SDNN/RMSSD ratio of the adjacent date (the day before or after) of a day is also in the top three, give 1 point to that date.

For the dates with the smallest HF % values within the ovulation interval, give 3, 2, 1 points respectively. If the HF % value of the adjacent date (the day before or after) of a day is also in the top three, give 1 point to that date.

For the dates with the biggest LF/HF ratio within the ovulation interval, give 3, 2, 1 points respectively. If the LF/HF ratio of the adjacent date (the day before or after) of a day is also in the top three, give 1 point to that date.

After the above scoring, add up the scores of each day within the ovulation interval, and the date with the highest score is considered the most likely ovulation date. The following describes the female physiological period ovulation detection system 100.

Figure 4:
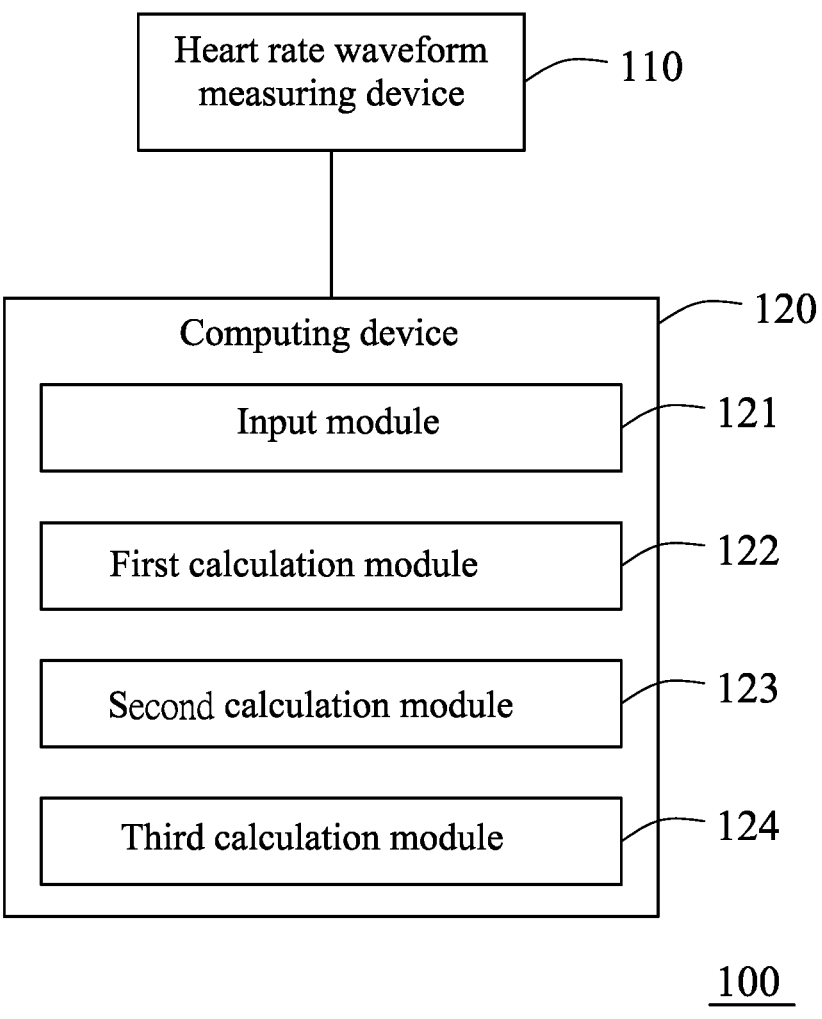
FIG. 4 a schematic diagram of the female physiological period ovulation detection system 100; and FIG. 5

Please refer to FIG. 4, which is a schematic diagram of the female physiological period ovulation detection system 100. The female physiological period ovulation detection system 100 is configured for application to a subject. The female physiological period ovulation detection system 100 includes at least one heart rate waveform measuring device 110 and a computing device 120. The heart rate waveform measuring device 110 can provide a heart rate waveform signal. This can be a wearable device, such as a heart rate bracelet, a heart rate watch or other forms of heart rate monitors. Further, it measures the heart rate waveform signal from the subject's body through contact or non-contact methods.

The computing device 120, for example, a personal computer or a smartphone, is connected to the heart rate waveform measuring device 110. The computing device 120 includes an input module 121, a first calculation module 122, a second calculation module 123, and a third calculation module 124.

The input module 121 is configured for inputting the first day of the physiological period, the longest cycle length of the physiological period, and the shortest cycle length of the physiological period. This information can be input by the subject himself, or automatically collected by the system. The first calculation module 122 is configured for calculating the ovulation interval date based on the input first day of the physiological period, the longest cycle length of the physiological period, and the shortest cycle length of the physiological period. The calculation method can refer to the aforementioned step S120.

The second calculation module 123 is configured for calculating the first cumulative power (LF), the second cumulative power (HF), the standard deviation of the heartbeat interval (SDNN), the root mean square of the adjacent difference sum of squares (RMSSD), the cumulative power ratio (LF/HF) and the heart rate parameter ratio (SDNN/RMSSD) based on the heart rate waveform signal. The calculation method can refer to the aforementioned steps S140, S141~S146, S150.

The third calculation module 124 is configured for calculating the ovulation day from the ovulation interval date based on the cumulative power ratio (LF/HF) and the heart rate parameter ratio (SDNN/RMSSD). The calculation method can refer to the aforementioned step S160.

The female physiological period ovulation detection system 100 can be integrated into a smartphone APP, a smart bracelet or other smart wearable devices, providing convenient and real-time ovulation day judgment results. The following will explain the actual experimental results.

Figure 5:
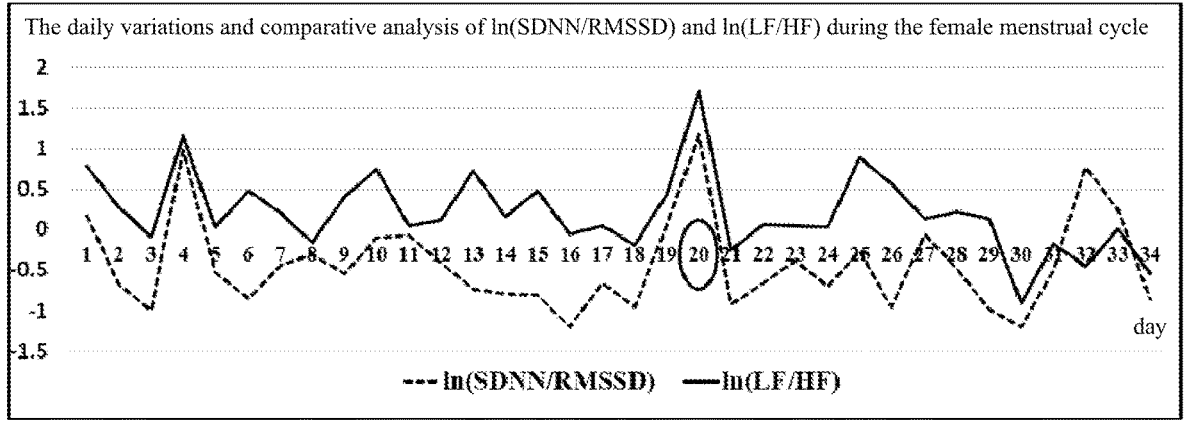
Figure 6:
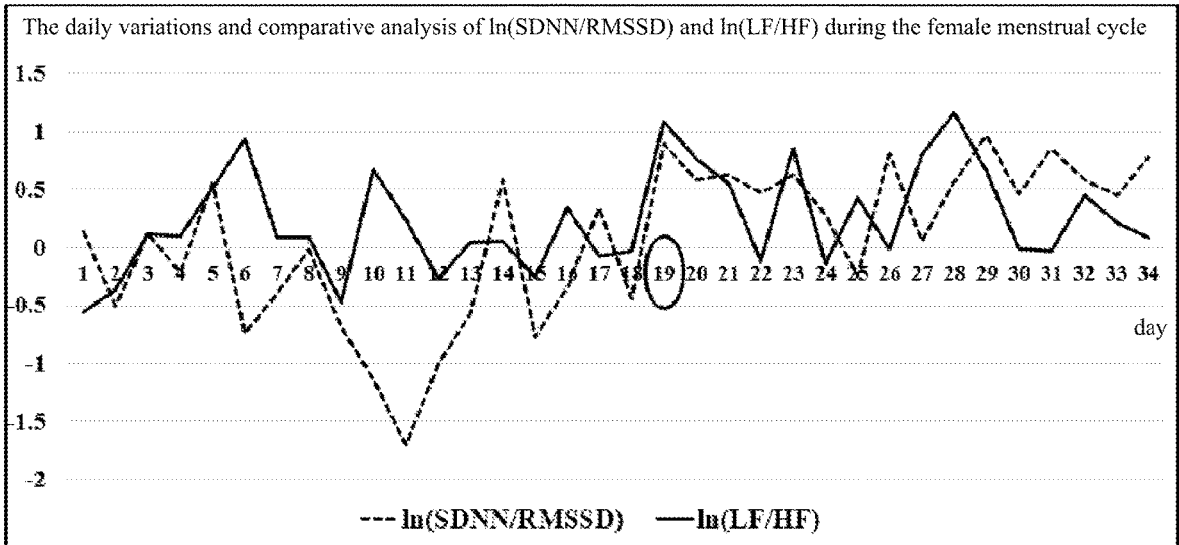
FIG. 6 illustrates actual test results.

Please refer to FIGS. 5 and 6, which are the actual test results. The inventor arranged for two subjects to test, measured their own heart rate waveform signals when they got up in the morning every day, further used the aforementioned method to calculate SDNN, RMSSD, RMSSD %, (SDNN/RMSSD) and LF %, HF %, (LF/HF), and recorded these data daily. At the same time, ovulation test paper was used to verify the test results.

The experimental data of the first subject showed that within the estimated ovulation interval date (the 13th to 23rd day), the maximum values of SDNN/RMSSD and LF/HF appeared on the 20th day, and the verification result of the ovulation test paper also confirmed that this day was the ovulation day.

For the second subject, the experimental results also showed a similar pattern. The estimated ovulation interval date was the 13th to 23rd day, and the maximum values of SDNN/RMSSD and LF/HF appeared on the 19th day, and this day was indeed the ovulation day verified by the ovulation test paper. This result further verifies the reliability of this method.

It is worth noting that although the LF/HF value on the 28th day is greater than that on the 19th day, and the SDNN/RMSSD on the 29th day is greater than that on the 19th day, but because these two days are not within the estimated ovulation interval date, and they do not meet the condition that both indicators are the maximum values at the same time, they are not misjudged as ovulation days.

The female physiological period ovulation detection method of the present invention uses physiological parameters of heart rate waveform signals, such as the standard deviation of heartbeat intervals (SDNN), the root mean square of the sum of squares of adjacent differences (RMSSD), and the frequency domain parameters of heart rate variability LF, HF, to test the ovulation day through the changes and ratios of these parameters. It can effectively improve the accuracy of ovulation day testing, is non-invasive, and is convenient for users to understand their own physiological conditions, and has high practicality and convenience.

A number of implementations have been described. Nevertheless, it will be understood that various modifications may be made without departing from the spirit and scope of the disclosure. Accordingly, other implementations are within the scope of the following claims.

Although the description above contains many specifics, these are merely provided to illustrate the invention and should not be construed as limitations of the invention's scope. Thus, it will be apparent to those skilled, in the art that various modifications and variations can be made in the system and processes of the present disclosure without departing from the spirit or scope of the invention.

What is claimed is:

1. A method for detecting ovulation in a female's menstrual cycle, comprising the steps of:
   (a) obtaining, with a computing device, the first day of a subject's menstrual cycle, longest cycle length and shortest cycle length;
   (b) calculating, with a computing device, an ovulation interval based on the longest and shortest cycle lengths;
   (c) measuring daily, with a heart rate waveform measuring device, a heart rate waveform signal of the subject;

for each heart rate waveform signal:

(d) from the heart rate waveform signal, determining, with the computing device, a first cumulative power (LF), a second cumulative power (HF), a standard deviation of interbeat intervals (SDNN), and a root mean square of successive differences (RMSSD), wherein a sampling frequency range of the second cumulative power is greater than that of the first cumulative power; and (e) determining, with the computing device, a cumulative power ratio (LF/HF) by dividing the first cumulative power by the second cumulative power, and a heart rate parameter ratio (SDNN/RMSSD) by dividing the standard deviation of interbeat intervals by the root mean square of successive differences; and (f) selecting, with the computing device, a day within the ovulation interval where both the cumulative power ratio (LF/HF) and the heart rate parameter ratio (SDNN/RMSSD) are at their maximum as the day of ovulation.

2. The method for detecting ovulation in a female's menstrual cycle of claim 1, further comprising the steps of:

for each heart rate waveform signal:

(d1) preprocessing the heart rate waveform signal;

(d2) obtaining interval times between adjacent peaks in the heart rate waveform signal to form a time series;

(d3) based on the time series, calculating the standard deviation of interbeat intervals (SDNN) and the root mean square of successive differences (RMSSD);

(d4) resampling the time series to obtain an equidistant time series;

(d5) transforming the equidistant time series to obtain power spectrum information; and (d6) obtaining the first cumulative power (LF) and the second cumulative power (HF) from the power spectrum information, wherein the sampling frequency range of the second cumulative power is greater than that of the first cumulative power.

3. The method for detecting ovulation in a female's menstrual cycle of claim 2, wherein the sampling frequency range of the first cumulative power is 0.04-0.15 Hz, and the sampling frequency range of the second cumulative power is 0.15-0.4 Hz.

4. The method for detecting ovulation in a female's menstrual cycle of claim 2, further comprising sampling a third cumulative power (TF) with a sampling frequency range of 0.04-0.4 Hz, and calculating a percentage of the first cumulative power (LF %) and the second cumulative power (HF %) as follows:

$$\text{"}LF\% = LF/TF \times 100\%\text{"};$$

$$\text{"}HF\% = HF/TF \times 100\%\text{"}.$$

5. The method for detecting ovulation in a female's menstrual cycle of claim 2, wherein in step (d4), the resampling of the time series is performed using the Berger algorithm.

6. The method for detecting ovulation in a female's menstrual cycle of claim 2, wherein in step (d5), the transformation of the equidistant time series is performed using the Discrete Fourier Transform.

7. The method for detecting ovulation in a female's menstrual cycle of claim 1, wherein if the longest and shortest menstrual cycle lengths cannot be obtained from the subject, the longest cycle length is considered as 35 days, and the shortest cycle length as 21 days.

8. The method for detecting ovulation in a female's menstrual cycle of claim 1, wherein in step (b), the start date of the ovulation interval is determined by subtracting 18 days from the shortest cycle length, and the end date of the ovulation interval is determined by subtracting 11 days from the longest cycle length.

9. A system for detecting ovulation in a female's menstrual cycle, applicable to a subject, comprising:

at least one heart rate waveform measuring device, configured for providing a heart rate waveform signal; and a computing device connected to the heart rate waveform measuring device, including:

an input module, configured for inputting the first day of a menstrual cycle, and longest and shortest cycle lengths;

a first calculating module, configured for calculating an ovulation interval based on the first day, and the longest and shortest cycle lengths;

a second calculation module, configured for calculating a first cumulative power (LF), a second cumulative power (HF), a standard deviation of interbeat intervals (SDNN), a root mean square of successive differences (RMSSD), a cumulative power ratio (LF/HF), and a heart rate parameter ratio (SDNN/RMSSD) based on the heart rate waveform signal; and a third calculation module, configured for selecting an ovulation day within the ovulation interval based on the cumulative power ratio (LF/HF) and the heart rate parameter ratio (SDNN/RMSSD), wherein the third calculation module selects a day with the maximum values of both ratios as the ovulation day.

10. The system for detecting ovulation in a female's menstrual cycle, applicable to a subject of claim 9, wherein the second calculation module preprocesses the heart rate waveform signal to obtain a time series, calculates the standard deviation of interbeat intervals (SDNN) and the root mean square of successive differences (RMSSD), resamples and converts the time series to obtain power spectrum information, and from the power spectrum information, obtains the first cumulative power (LF) and the second cumulative power (HF), wherein a sampling frequency range of the second cumulative power is greater than that of the first cumulative power.

* * * * *